(12) United States Patent
Cole et al.

(10) Patent No.: US 8,651,737 B2
(45) Date of Patent: Feb. 18, 2014

(54) SENSOR TEMPERATURE SENSING DEVICE

(75) Inventors: Barrett E. Cole, Bloomington, MN (US); Robert Higashi, Shorewood, MN (US); Peter Tobias, Minneapolis, MN (US)

(73) Assignee: Honeywell International Inc., Morristown, NJ (US)

( * ) Notice: Subject to any disclaimer, the term of this patent is extended or adjusted under 35 U.S.C. 154(b) by 131 days.

(21) Appl. No.: 12/821,637

(22) Filed: Jun. 23, 2010

(65) Prior Publication Data
US 2011/0317739 A1 Dec. 29, 2011

(51) Int. Cl.
*G01K 7/00* (2006.01)

(52) U.S. Cl.
USPC .......................................... 374/185; 374/183

(58) Field of Classification Search
USPC ........................................ 374/183, 185, 163
See application file for complete search history.

(56) References Cited

U.S. PATENT DOCUMENTS

| | | | |
|---|---|---|---|
| 2004/0178069 A1* | 9/2004 | Wang et al. | 204/408 |
| 2006/0267724 A1* | 11/2006 | Parsons | 338/25 |
| 2009/0159445 A1* | 6/2009 | Krishna et al. | 204/424 |
| 2009/0312954 A1* | 12/2009 | Utriainen | 702/23 |

* cited by examiner

*Primary Examiner* — Mirellys Jagan
(74) *Attorney, Agent, or Firm* — Brooks, Cameron & Huebsch, PLLC

(57) ABSTRACT

The present disclosure includes sensing device embodiments. One sensing device includes a heater layer, a resistance detector layer, constructed and arranged to indicate a temperature value based upon a correlation to a detected resistance value, an electrode layer, and a sensing layer.

14 Claims, 4 Drawing Sheets

SENSOR TEMPERATURE SENSING DEVICE

BACKGROUND

The present disclosure is related generally to the field of temperature sensors. More particularly, the present disclosure is related to temperature sensors for use on sensing devices.

In some applications, sensing devices are constructed using a metal oxide semiconductor (MOS) resistive sensing material on a thermally isolated microbridge structure (BRIDGE), for example, as the structure for a MOSBRIDGE fire sensor. As will be understood by those of ordinary skill in the art, resistance circuits can be used to measure resistance and that resistance can be indicative of various qualities affecting the circuit.

When a fire starts, the combustion activity produces gases that can be detected by sensing devices. These fire sensing devices are used to measure a change in the gases around the sensing device. This can be beneficial, in some situations, for example where a change in gas can be detected before other signs of fire have occurred in the vicinity, like particulates production in smoke or a significant increase in temperature.

For example, with respect to fire sensing, a MOSBRIDGE based sensing device can be used to interact with gases around the MOSBRIDGE sensor. The sensor can be fabricated from materials that interact with the gases such that some of the gases produced can change the resistance of the material forming the sensor (e.g., the MOS of the MOSBRIDGE).

This change in resistance can be used to identify a changing gas environment around the fire sensor thereby indicating that a fire is changing the gas environment. However, heating of the sensor material can also create a similar resistance condition, and may lead to erroneous fire indication, in some instances.

Typically such devices utilize a material that needs to be heated in order to optimize its sensitivity. In order to heat the material, such devices typically utilize a platinum heating element. One approach to identifying the temperature of the sensing material is to monitor the heating element to determine the temperature of the sensor. However, in some situations, electro-migration from the temperature sensor may disable or destroy the heater. This is particularly true in situations where the devices are miniaturized. For example, a sensor with an area of around 20 microns may have such characteristics although this disclosure is not limited to such sizes.

To remedy this issue, Nickel-Chromium heaters could be used as a substitute for the platinum heaters, but these heaters have low temperature coefficients of resistivity and, therefore, monitoring the heater's resistivity to determine temperature of the sensor may be problematic in some situations.

In designs, the heater can be fabricated having a number of conducting legs extending away from the central portion of the device. Accordingly, these legs provide a portion of the resistance attributable to the heater layer and therefore the heater layer has only a portion of its resistance in the area proximate to the sensing material (e.g., central heated zone of the device) and so changes in the temperature of the heater may not be accurate.

Additionally, this central zone can be small (e.g., 20 microns×20 microns) in some device configurations and, as such, temperature changes can occur quickly thereby making measurement of the heater unreliable in some applications. However, having such a small sensing area can allow for the sensing device to operate under a low power level (e.g., under 10 milliwatts, in some applications) versus other larger devices and therefore, such devices could be useful.

DETAILED DESCRIPTION

Figure 1:
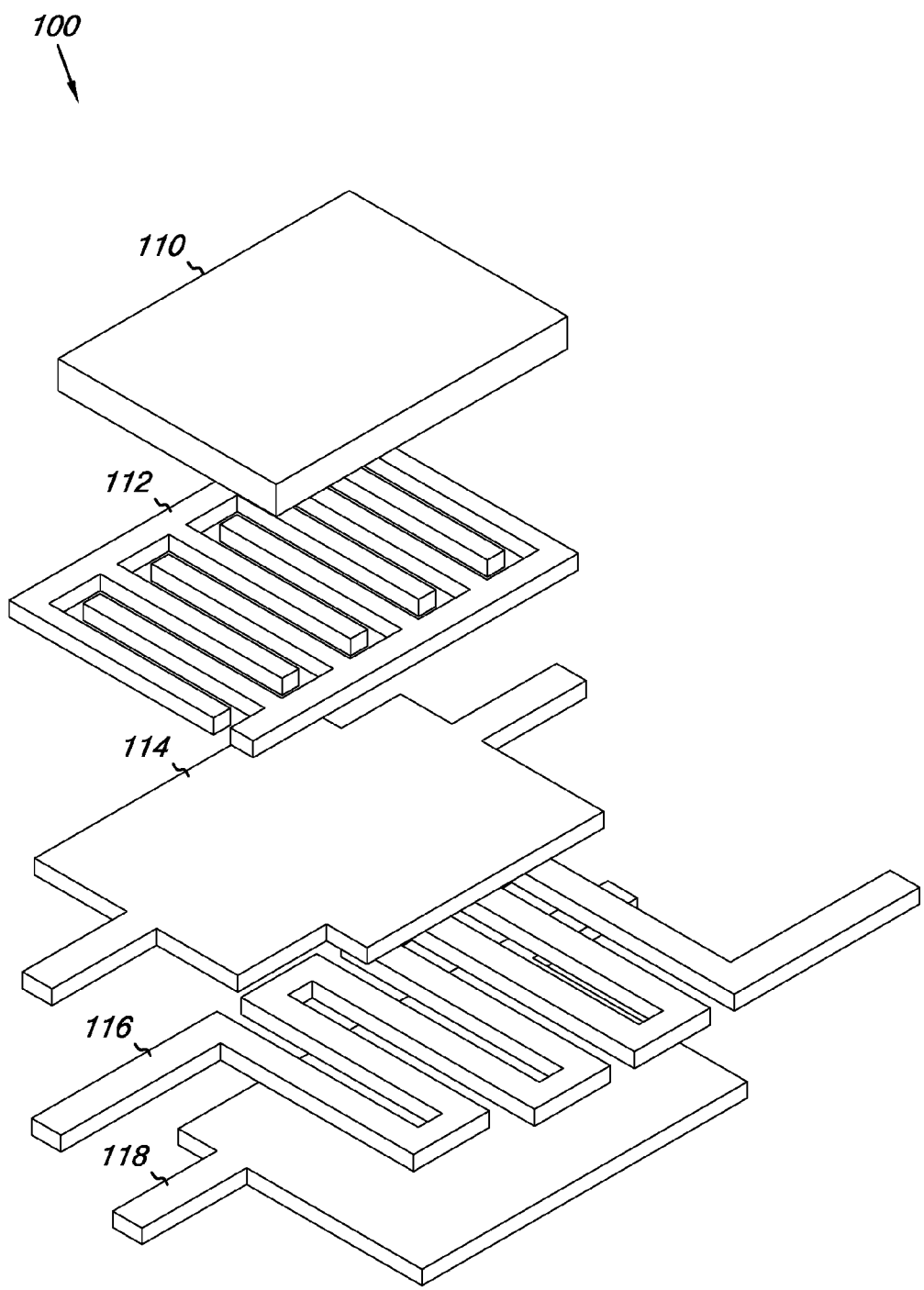
FIG. 1 illustrates an embodiment of a sensing device having a resistance temperature detector.

In the following detailed description of the present disclosure, reference is made to the accompanying drawings that form a part hereof, and in which is shown by way of illustration how one or more embodiments of the disclosure may be practiced. These embodiments are described in sufficient detail to enable those of ordinary skill in the art to practice the embodiments of this disclosure, and it is to be understood that other embodiments may be utilized and that process, electrical, and/or structural changes may be made without departing from the scope of the present disclosure.

Based upon the above discussion, it may be helpful to know the temperature and/or change in temperature of a sensor (e.g., MOSBRIDGE) in order to understand what its resistance should be based upon that temperature. This may be helpful, for example, in some instances, to measure the temperature of the fire sensor in order to identify whether a change in the resistance of the MOSBRIDGE is due to a temperature change of the MOSBRIDGE or a change in the gas environment. The present disclosure provides embodiments utilized for measuring the temperature of a sensor.

In some embodiments, a resistance change in a sensing material, such as, chromium titanium oxide sensing material, is differentiated from a change in temperature of the material. Fire sensors also, typically, are heated using a heater component of the sensing device structure.

Such changes in the resistance of the chromium titanium oxide material at elevated temperatures of, for example, 300-400 degrees C. are used to indicate the presence of changes in the gas environment that are caused by a fire. This is because chromium titanium oxide has a large change in resistance as it is heated, changing by 3-4 decades between room temperature and 400 degrees C.

Accordingly, metal oxide semiconductor sensors can typically be heated to temperatures of up to 300-400 degrees C. for best sensing. At these temperatures, the material is often at its most reactive.

If the temperature of the sensing material on the fire sensor is measured, in some embodiments, the temperature of the sensing material can be controlled (e.g., by adjusting the heat generated by the heater) so that resistance changes caused by sensing material temperature changes are not interpreted as a change in the gas environment. Such an ability to control the temperature can be beneficial, for example, because it can provide repeatable conditions from device to device for better manufacturability. It also can be a desirable feature, in some applications, for the temperature measurement to be absolute, which embodiments described herein in FIGS. 1-3B. An absolute temperature would be beneficial, for example, in calibrating the device, for instance, if the substrate should heat up during a fire or exposure to a heat source.

Further, as discussed above, the materials forming the resistance detection layer with respect to the embodiments of FIGS. 1-3B, typically can withstand high (e.g., 700-900 degrees C.) anneal temperatures and may thereby be beneficial in some fabrication situations.

Figure 4:
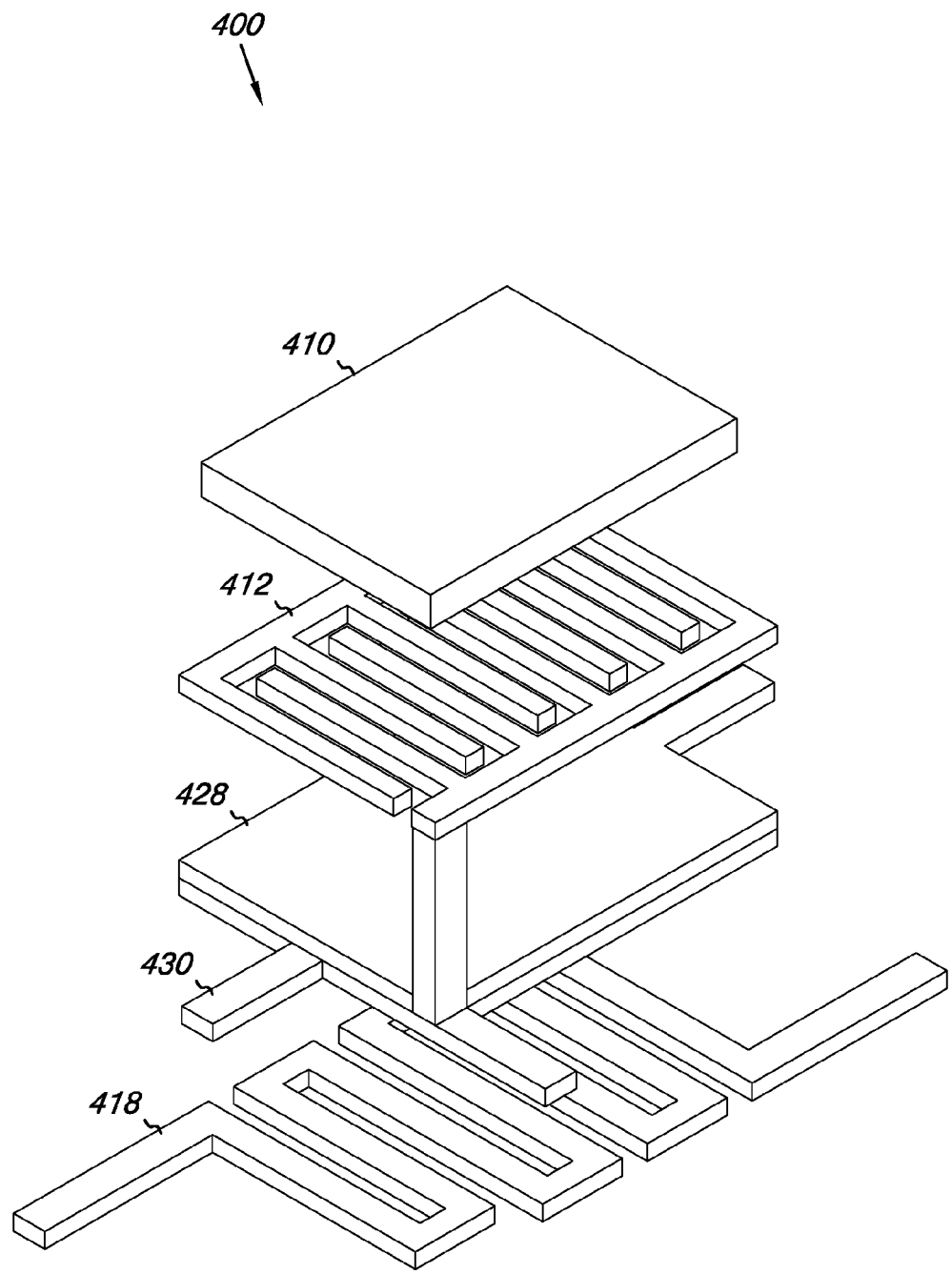
FIG. 4 illustrates an embodiment of a sensing device having a thermocouple resistance temperature detector.

Thermocouple embodiments, such as that illustrated in FIG. 4 can provide a temperature measurement that is relative to a junction between the materials of the thermocouple. For example, when a thermocouple is utilized in the structure of a fire sensor, the thermocouple is typically positioned on or above a heater portion (e.g., a heater layer of, for example, nickel/chromium (NiCr)) of the fire sensor.

In some implementations, the thermocouple has two dissimilar metals deposited on top of each other to form a junction (e.g., chromium (Cr) and Nickel/Iron (NiFe)). This type of implementation can provide a relatively large Seebeck voltage, in some designs. In such implementations, the thermocouple utilizes a cold junction on a substrate which can provide a sensing material temperature relative to the substrate temperature. For measuring the absolute temperature of the sensing material, a sensor at the substrate could measure the substrate temperature.

In some embodiments of the present disclosure, a semi-conductive material is deposited between two leads. Cr is a suitable material that can be utilized in forming the leads. In such embodiments, resistance changes in the semi-conductive material can be used to determine the temperature of the sensing material.

The semi-conductive material and resistance can be selected so that most of the resistance change is proximate to sensor material and not on the conducting legs. Such a design also can maintain a ground plane between the heater below the sensing material (e.g., chromium titanium oxide) located above to, for example, isolate the voltages.

As will be appreciated, elements shown in the various embodiments herein can be added, exchanged, and/or eliminated so as to provide a number of additional embodiments of the present disclosure. In addition, the proportion and the relative scale of the elements provided in the figures are intended to illustrate various embodiments of the present invention and are not to be used in a limiting sense.

FIG. 1 illustrates an embodiment of a sensing device having a resistance temperature detector. In some embodiments, the sensing device is configured to sense change in a gas environment indicative of a fire being present.

The embodiment of FIG. 1 is one such embodiment and includes a sensing device 100 having a heater layer 116, a resistance detector layer, constructed and arranged to indicate a temperature value based upon a correlation to a detected resistance value 114, an electrode layer 112, and a sensing layer 110. In this embodiment, the resistance detector layer 114 is positioned between the heater 116 and the sensing layer 110.

In this way the resistance detector layer 114 can act as a shielding layer for the sensing layer 110. In some embodiments, the resistance detector layer 114 can act as a voltage shield for the sensing layer 110 from the voltage of the heater 116 that may affect the sensing capabilities of the sensing layer 110.

In various embodiments, the sensing layer is formed from a chromium titanium oxide material. This material can be beneficial for some applications, such as fire sensing, in that the chromium titanium oxide can be heated to, for example, 300-400 degrees C. during operation and thereby can indicate the presence of changes in the gas environment that are caused by a fire.

As discussed above, this is because chromium titanium oxide has a large change in resistance as it is heated, changing by 3-4 decades between room temperature and 400 degrees C. Accordingly, in some embodiments, the heater can be controlled to maintain an operating temperature of approximately 300-400 degrees C. and this temperature can be adjusted based upon the resistance detected by the resistance detector layer.

In some embodiments, the other layers of the sensing device can utilize different materials. For example, the heater layer can be formed from a nickel chromium material, among other suitable materials.

Further, in some embodiments, grounding the electrode 112 can keep any stray voltages from the heater below from effecting the resistance measurement of the sensing layer material (e.g., chromium titanium oxide material).

In various embodiments, the resistance detector layer is formed utilizing a silicon based semi-conductive material layer. As discussed above, this may be a semi-conductive material layer and the layer may shield the sensing layer from voltage from the other layers of the sensing device illustrated in the embodiment of FIG. 1 and/or other components of the sensing device.

In some embodiments, a semi-conductive material layer is formed from a silicon based material, such as, for example, a material layer formed utilizing silicon nitride.

Silicon based embodiments may be beneficial, in some instances, because embodiments can be stable to higher temperatures and provide sensitivity for small temperature changes.

In the various embodiments disclosed herein, the layers described can be placed in various orders that are not shown in the drawings, but will be understood by the reader of the disclosure. In some embodiments, each layer overlaps with each neighboring layer to more than 50% overlap, and no pair of the layers are placed side by side. This can be beneficial, in some instances because the arrangement allows a very compact design, compared to gas sensor and temperature sensor side-by-side implementation.

The resistance detector layer can take a number of suitable shapes. For example, in some embodiments where the resistance detector layer is silicon based, the resistance detector layer can be substantially planar.

In various embodiments, a number of passivation layers 118 may be utilized. For example, in some embodiments, one or more passivation layers may be positioned below the heater 116, as shown, between the heater 116 and the resistance detector layer 114, and/or between the resistance detector layer 114 and the electrode layer 112. These passivation layers may act as insulators that insulate the voltage of one layer with respect to an adjacent layer or component.

In some embodiments, the heater layer is placed between the sensing layer and the resistance detector layer. The resistance detector layer, then 118, could not serve as an electric shield in this embodiment, but the more compact design still allows sensing devices with lower power consumption, in some such embodiments. In some embodiments, the resistance detector layer shields the electrode and/or sensing layers from electrical interference from the heater layer as described herein.

And, as described in more detail below with respect to FIG. 2, in some embodiments, such as those formed utilizing a metal or a metal alloy, the resistance detector layer can a serpentine shaped layer. For example, the resistance detector layer can be formed from a thin metal film layer of platinum. In some instances, a serpentine shape can offer benefits such as being easier to manufacture, simpler ohmic contact formation, and a desirable temperature compatibility with the sensing layer, among other benefits.

Figure 2:
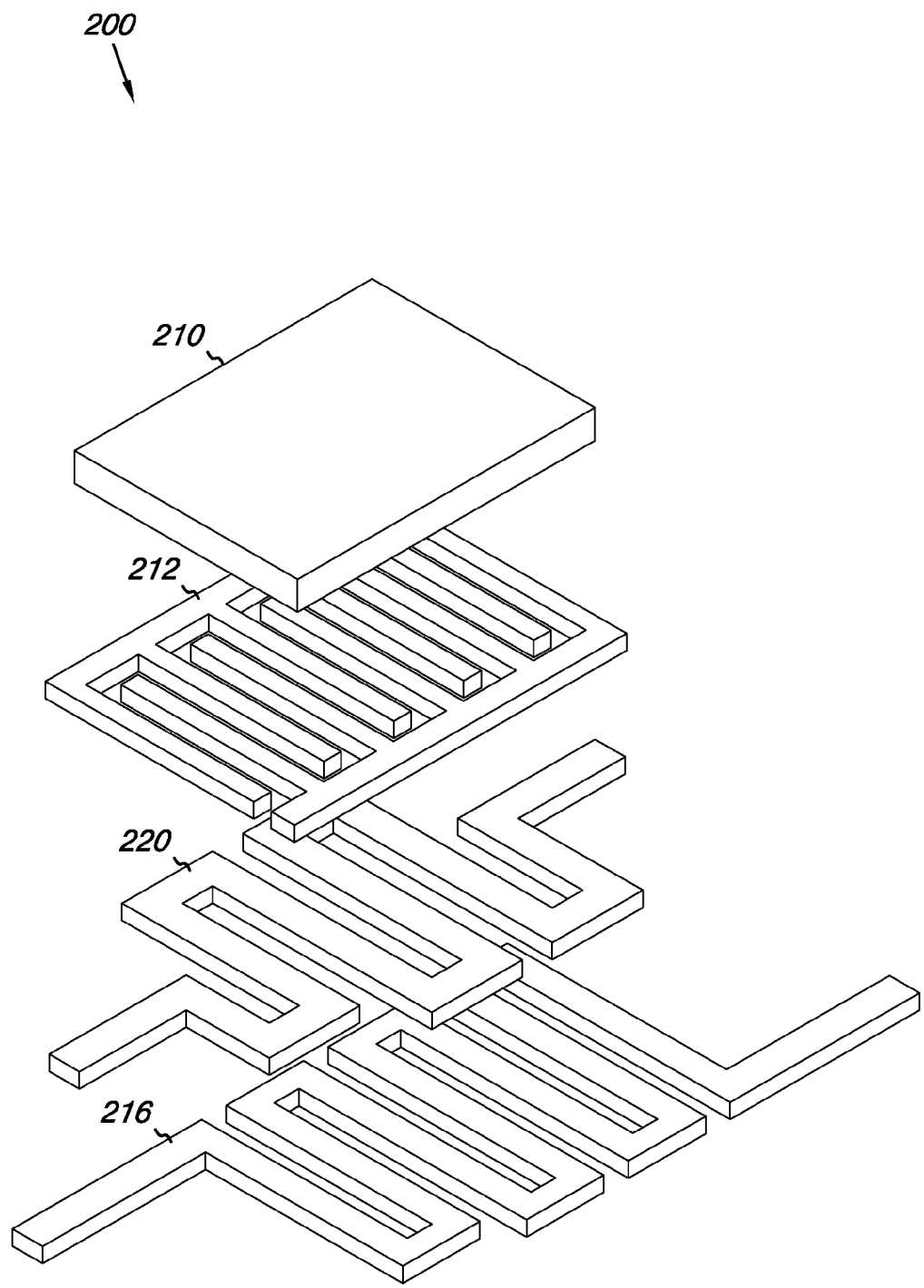
FIG. 2 illustrates an embodiment of a sensing device having a metal film resistance temperature detector.

FIG. 2 illustrates an embodiment of a sensing device having a metal film resistance temperature detector. The figures herein follow a numbering convention in which the first digit or digits correspond to the drawing figure number and the remaining digits identify an element or component in the drawing.

Similar elements or components between different figures may be identified by the use of similar digits. For example, 110 may reference element "10" in FIG. 1, and a similar element may be referenced as 210 in FIG. 2.

The embodiment of FIG. 2 includes a sensing device 200 having a heater layer 216, a serpentine shaped resistance detector layer 220, constructed and arranged to indicate a temperature value based upon a correlation to a detected resistance value, an electrode layer 212, and a sensing layer 210. As with the structure of FIG. 1, in this embodiment, the resistance detector layer 220 is positioned between the heater 216 and the sensing layer 210. However, in the embodiment of FIG. 2, the resistance detector layer 220 is formed in a serpentine shape.

The serpentine shape may provide less shielding than some substantially planar embodiments. However, as discussed above, in some instances, a serpentine shape can be beneficial as it may be easier to manufacture, provide simpler ohmic contact formation, and a desirable temperature compatibility with the sensing layer, among other benefits. One example embodiment of a sensing device includes a nickel chromium heater layer, an electrode layer, a serpentine shaped resistance detector layer, and a chromium titanium oxide sensing layer.

In some embodiments, the serpentine shaped resistance detector layer is formed utilizing platinum. In various embodiments, the electrode layer is formed utilizing at least one of platinum, chromium titanium oxide, and gold. Those of ordinary skill in the art will understand that other suitable materials can be utilized in forming the electrode layer.

Figure 3A:
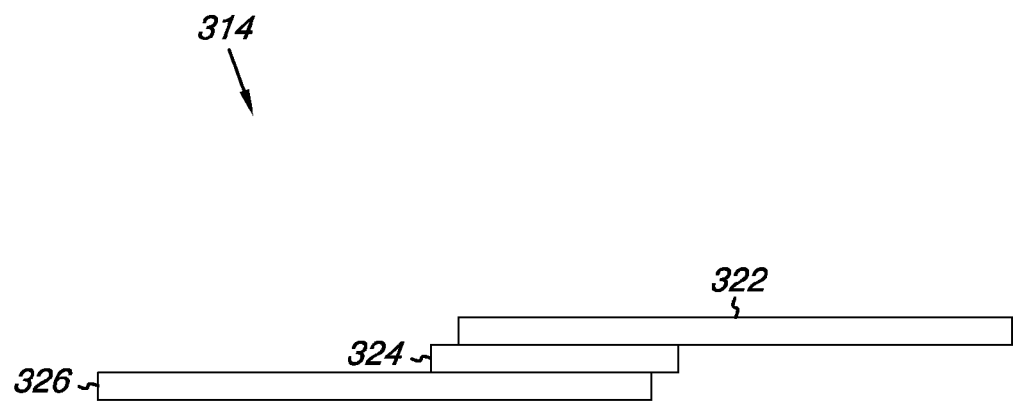
FIG. 3A is a side view of a silicon structure that can be utilized in embodiments of the present disclosure.

FIG. 3A is a side view of a silicon structure that can be utilized in embodiments of the present disclosure. In various embodiments, the resistance detector layer includes a layered structure 314 having semi-conductive material layer 324 located between two conductive material layers 322 and 326.

In some embodiments, the conductive material layers can be utilized as electrical leads with the semi-conductive material located between the two leads. The conductive material layers can be formed utilizing the same material or can be formed utilizing different materials.

Cr is one suitable material because of its ability to be exposed to a higher range of temperatures than some other suitable materials. This can be beneficial, for example, because Cr can withstand an annealing process having temperatures in the 700-800 degree C. range which is not the case with NiFe used in some sensing device fabrication techniques. Pt is also another possibility as it may form better ohmic contact to the silicon (Si) of the semi-conductive material than other materials.

The semi-conductive layer can be selected from a number of materials such as Si based materials (e.g., hydrogenated amorphous silicon which gets conductive at higher temperatures than some other Si based materials or other semi-conductive materials). In some embodiments, it is desirable for the material to have kilohm range resistance in the operating region of 300-500 degrees C. for improved results.

Figure 3B:
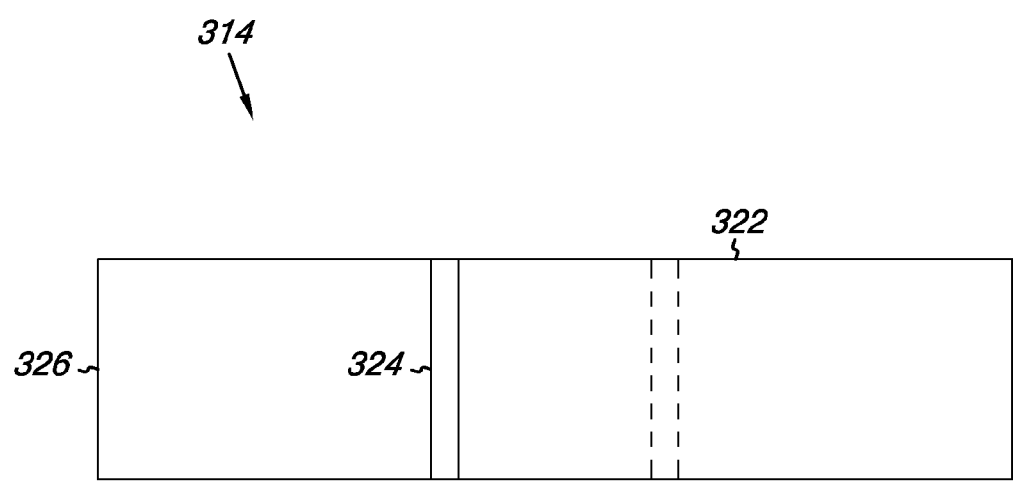
FIG. 3B is a top view of the silicon structure of FIG. 3A.

Embodiments, such as that illustrated in FIGS. 3A and 3B, include layers 322, 324, and/or 326 of the layered structure 314. As shown in FIGS. 3A and 3B, in some embodiments, two or more of these layers can be offset with respect to one another. For example, in various embodiments, the layers of the layered structure 314 are offset such that a first layer 322 has an end that overlaps a first end of a second layer 324 and a portion of the first layer 322 that does not overlap second layer 324 and a third layer 326 has an end that overlaps a second end of the second layer 324 and a portion of the third layer 326 that does not overlap the second layer 324.

As discussed above, in some embodiments, the conductive layers 322 and 326 of the layered structure 314 are formed utilizing the same conductive materials. For example, in some embodiments, the conductive layers 322 and 326 can be formed utilizing platinum, chromium, or another suitable conductive layer material.

In some embodiments, the conductive layers 322 and 326 of the layered structure 314 are formed from two different conductive materials. For example, in various embodiments, one of the conductive layers 322 or 326 is formed utilizing platinum and the other formed utilizing chromium.

FIG. 3B is a top view of the silicon structure of FIG. 3A. As shown in the embodiment of FIGS. 3A and 3B, the resistance detector layer can, in some embodiments, include a layered structure 314 wherein the layered structure has a semi-conductive material layer 324 located between two conductive material layers 322 and 326. Also, as shown in FIG. 3A, two or more of layers 322, 324, and/or 326 of the layered structure 314 can be offset with respect to one another.

For example, in one embodiment, a sensing device includes a nickel chromium heater layer, a resistance detector layer, constructed and arranged to indicate a temperature value based upon a correlation to a detected resistance value, having a layered structure wherein the layered structure includes a semi-conductive material layer located between two conductive material layers, an electrode layer, and a chromium titanium oxide metal oxide semiconductor sensing layer. Some such embodiments may also be beneficial, in some instances, because embodiments can be stable to higher temperatures and provide sensitivity for small temperature changes.

Another structure that would be useful in detecting a temperature change in such a device could be a thermocouple. FIG. 4 illustrates an embodiment of a sensing device having a thermocouple voltage temperature detector. In the embodiment illustrated in FIG. 4, the device 400 includes a heater layer 418, a thermocouple detector layer having two portions, an upper portion 428 and a lower portion 430, constructed and arranged to indicate a temperature value based upon a correlation to a detected thermoelectric voltage value, an electrode layer 412, and a sensing layer 410.

A thermocouple is typically formed through the orientation of two dissimilar layers of material that, when heated, create a voltage that can be measured. Accordingly, although shown as a single layer in FIG. 4, the thermocouple layer 428 can be made up of multiple layers.

As those of ordinary skill in the art will understand, a Seebeck voltage is created due to the Seebeck effect, which is the production of a small voltage across one of the layers of material due to a difference in temperature along that material. This effect can be produced at a junction of two dissimilar conductive materials where the materials have a portion in contact. Each conductive material produces a different voltage, which translates to a voltage difference (Seebeck Voltage) between the two layers of material.

Most any pair of dissimilar conductive materials can produce a measurable voltage when their junction is heated. When a pair of dissimilar conductive materials is combined for the purpose of measuring temperature, the device formed is called a thermocouple. Materials that would be suitable for fire sensing applications include Nickel/Iron (NiFe) and/or Chromium.

Using thermocouple embodiments can be advantageous in some situations. For example, thermocouple embodiments can operate at low voltage and therefore interference with the sensing layer 410 can be reduced, among other benefits.

The embodiments described herein can also perform at low power and can be designed having a small form factor. These characteristics can be advantageous in some situations. For example, some embodiments described herein can operate with a ratio of 1 mW/20 degrees C. (e.g., 20 mW/400 degrees C.). Such a ratio can be helpful in providing accurate sensing of the device. This characteristic can be helpful in allow the device to be made in small form factors (e.g., 20 microns×20 microns).

Although specific embodiments have been illustrated and described herein, those of ordinary skill in the art will appreciate that any arrangement calculated to achieve the same techniques can be substituted for the specific embodiments shown. This disclosure is intended to cover any and all adaptations or variations of various embodiments of the disclosure.

As used herein, the term "and/or" includes any and all combinations of one or more of the associated listed items. It will be understood that, although the terms first, second, etc. may be used herein to describe various elements and that these elements should not be limited by these terms. These terms are only used to distinguish one element from another element. Thus, a first element could be termed a second element without departing from the teachings of the present disclosure.

It is to be understood that the use of the terms "a", "an", "one or more", "a number of", or "at least one" are all to be interpreted as meaning one or more of an item is present. Additionally, it is to be understood that the above description has been made in an illustrative fashion, and not a restrictive one. Combination of the above embodiments, and other embodiments not specifically described herein will be apparent to those of skill in the art upon reviewing the above description.

The scope of the various embodiments of the disclosure includes any other applications in which the above structures and methods are used. Therefore, the scope of various embodiments of the disclosure should be determined with reference to the appended claims, along with the full range of equivalents to which such claims are entitled.

In the foregoing Detailed Description, various features are grouped together in example embodiments illustrated in the figures for the purpose of streamlining the disclosure. This method of disclosure is not to be interpreted as reflecting an intention that the embodiments of the disclosure require more features than are expressly recited in each claim.

Rather, as the following claims reflect, inventive subject matter lies in less than all features of a single disclosed embodiment. Thus, the following claims are hereby incorporated into the Detailed Description, with each claim standing on its own as a separate embodiment.

What is claimed:

1. A sensing device having a number of component layers provided therein, comprising:
   a heater layer;
   a resistance detector layer provided above the heater layer and constructed and arranged to indicate a temperature value based upon a correlation to a detected resistance value;
   an electrode layer provided above the resistance detector layer; and
   a sensing layer provided above the electrode layer, wherein the resistance detector layer includes a layered structure having a semi-conductive material layer located between two conductive material layers.

2. The sensing device of claim 1, wherein the sensing device is configured to sense change in a gas environment indicative of a fire being present.

3. The sensing device of claim 1, wherein the device provides 400 degrees C. of heat during operating sensing conditions.

4. The sensing device of claim 1, wherein the layers above can be placed in various orders, but each layer overlaps with each neighboring layer to more than 50% overlap, and no pair of the layers are placed side by side.

5. The sensing device of claim 1, wherein the resistance detector layer is a serpentine shaped layer.

6. The sensing device of claim 1, wherein the layers of the layered structure are offset with respect to one another.

7. The sensing device of claim 1, wherein the layers of the layered structure are offset such that a first layer has an end that overlaps a first end of a second layer and a portion of the first layer that does not overlap second layer and a third layer has an end that overlaps a second end of the second layer and a portion of the third layer that does not overlap the second layer.

8. A sensing device having a number of component layers provided therein, comprising:
   a nickel chromium heater layer;
   a resistance detector layer, provided above the heater layer and constructed and arranged to indicate a temperature value based upon a correlation to a detected resistance value, having a layered structure wherein the layered structure includes a semi-conductive material layer located between two conductive material layers;
   an electrode layer provided above the resistance detector layer; and
   a metal oxide semiconductor sensing layer provided above the electrode layer.

9. The sensing device of claim 8, wherein the semi-conductive material layer is formed from a silicon based material.

10. The sensing device of claim 8, wherein at least one of the conductive material layers is formed from platinum or chromium.

11. A sensing device having a number of component layers provided therein, comprising:
   a nickel chromium heater layer;
   an electrode layer provided above the heater layer;
   a serpentine shaped resistance detector layer, provided below the electrode layer constructed and arranged to indicate a temperature value based upon a correlation to a detected resistance value; and
   a chromium titanium oxide sensing layer provided above the electrode layer, wherein the detector layer shields the electrode and sensing layers from electrical interference from the heater layer.

12. The sensing device of claim 11, wherein the serpentine shaped resistance detector layer is formed utilizing platinum.

13. The sensing device of claim 11, wherein the heater layer is controlled to maintain an operating temperature of approximately 300-400 degrees C.

14. The sensing device of claim 11, wherein the electrode layer is formed utilizing at least one of platinum, chromium titanium oxide, and gold.

* * * * *